United States Patent [19]
Plate et al.

[11] Patent Number: 6,061,130
[45] Date of Patent: May 9, 2000

[54] APPARATUS FOR DETERMINING THE PARTICLE SIZE DISTRIBUTION OF A MIXTURE

[75] Inventors: Martin Plate, Langenfeld; Jürgen Pankratz, Giessen, both of Germany

[73] Assignee: F. Kurt Retsch GmbH & Co. KG, Germany

[21] Appl. No.: 09/234,980

[22] Filed: Jan. 22, 1999

[30] Foreign Application Priority Data

Jan. 22, 1998 [DE] Germany ............................ 198 02 141

[51] Int. Cl.⁷ ........................... G01N 15/02; G01N 15/14
[52] U.S. Cl. ............................................... 356/335; 377/11
[58] Field of Search .................................... 356/335, 338, 356/343; 377/11

[56] References Cited

U.S. PATENT DOCUMENTS 4,288,162  9/1981  Sakamoto et al. ...................... 356/335
5,011,285  4/1991  Jorgensen et al. ..................... 356/335
5,309,215  5/1994  Schumann .............................. 356/335

FOREIGN PATENT DOCUMENTS 41 19 240  12/1992  Germany .
97/14950    4/1997  WIPO .

Primary Examiner—Frank G. Font
Assistant Examiner—Layla Lauchman
Attorney, Agent, or Firm—Robert W. Becker & Associates

[57] ABSTRACT

An apparatus for determining the particle size distribution and for characterizing the particle shapes of a particle mixture has a metering device for classifying a particle mixture supplied in a particle stream to the apparatus. An optoelectronic measurement section is provided that has a light source and an image collecting device aligned with one another, wherein the particle stream is guided between the light source and the image collecting device. The image collecting device has a plurality of electrooptical image recording units directed onto the particle stream and having different image recording scales matched to one another to cover the whole measurement range of the apparatus. A computing unit converts digital image points recorded by the recording units into a size determination of the particles.

12 Claims, 1 Drawing Sheet

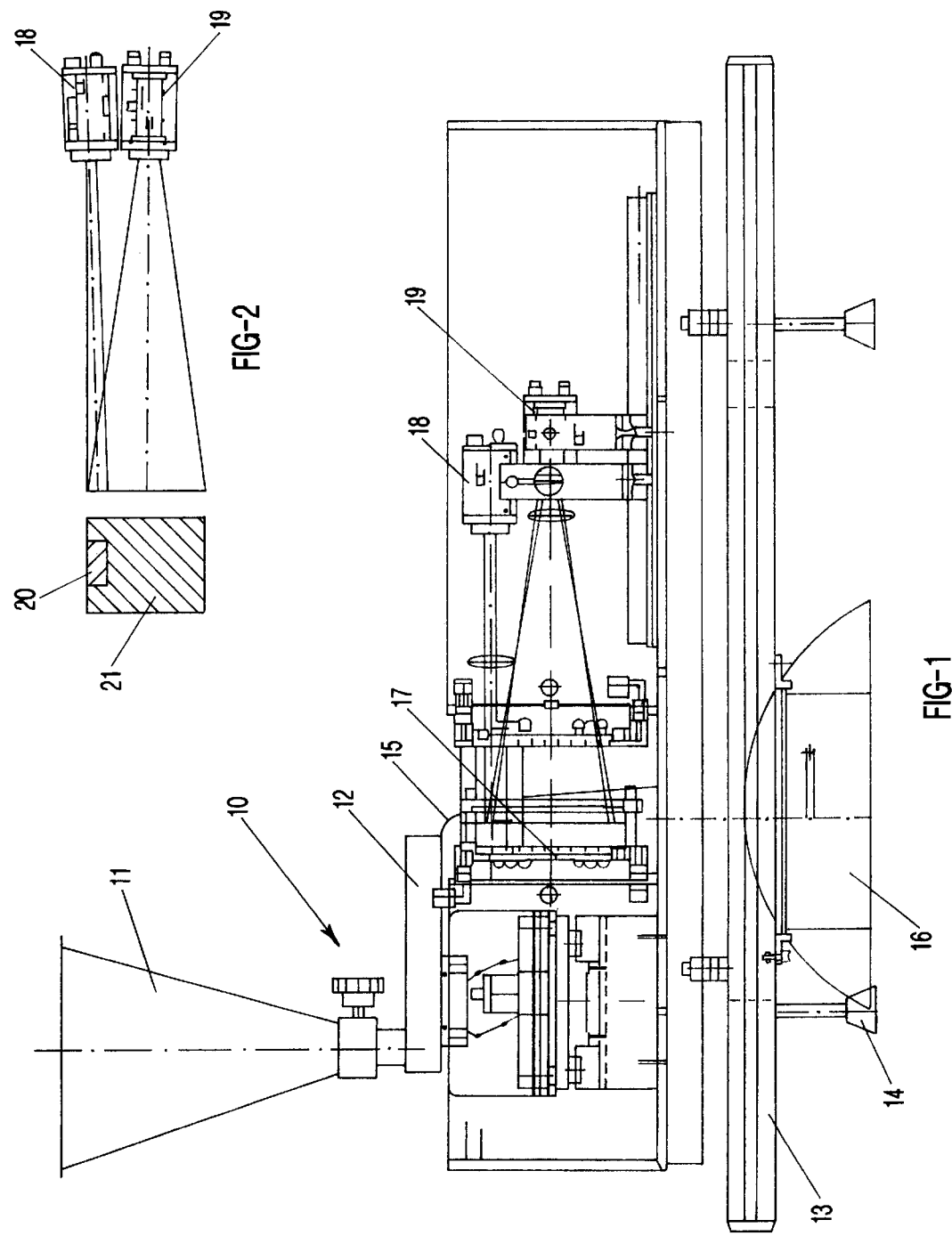

APPARATUS FOR DETERMINING THE PARTICLE SIZE DISTRIBUTION OF A MIXTURE

BACKGROUND OF THE INVENTION

The present invention relates to an apparatus for determining the particle size distribution and for characterising the particle shapes of a particle mixture by electrooptical scanning with a metering device for classifying the particle mixture in the particle stream to be scanned and with an optoelectronic measurement section formed by a light source and an image collecting device, along which section there takes place a movement effected by gravitational force or additional forces of the particle stream between the light source and image collecting device and a digital recording of the projection areas in the form of image points covered by the projection areas of the particles in the image collecting device, and with a computing unit for converting the digital information into a size determination of the recorded particles.

An apparatus of the aforementioned type is described in the company prospectus "Partikelform und Größenanalyse für Labor und Produktion" (Particle shape and size analysis for laboratory & production) published by Meßtechnik Schwarz GmbH, Düsseldorf. This apparatus includes a digital matrix camera that takes photographs, in the form of two-dimensional projection areas, of the particles moving through its image collecting area against the background of the light source, the accuracy of this recording being dependent on the exposure time and the depth of focus of the electrooptical image recording device that is used.

The so-called dynamic factor B, the quotient of the upper and lower measurement limits, serves as a measure of the measurement range of such a matrix camera. The larger for example the particles to be measured in the grain distribution to be investigated in the particle stream, the more image points there are covered by the particles in their passage through the image collection area of the matrix camera. Since within the scope of the computer-assisted evaluation all those particles are discounted that extend even only partially beyond the image collecting area, there is an increased probability that larger particles will be significantly under-represented in the investigation of corresponding grain distributions. In addition, larger and heavier particles have a higher fall velocity, with the result that, depending on the exposure time, there is the danger that the recorded projection area will be smudged. For the above reasons the dynamic factor is limited to B=35 to 40 with the widely employed CCD matrix cameras, so that in practice with a lens only those grain distributions having the necessary predictive accuracy can be investigated, in which the largest particle is at most 35–40 times as large as the smallest particle. If grain distributions having a width differing from the above or with another size range are to be investigated, then the image scale of the matrix camera must be matched to that of the grain distribution being investigated, which involves time-consuming and complicated manual activities such as changing lenses, adjusting the depth of focus, changing the camera position, and also adjusting the apparatus.

An apparatus of the aforedescribed type having an area camera is furthermore known from WO 97/14950 A1.

In an apparatus known from DE 41 19 240 C2 the image collecting device comprises a CCD line camera; since a line camera in each case records only the image of one chord length of the recorded particle, in order to obtain evaluable particle information the lines must be read in quick succession, in each case two-dimensional projection areas of the particles to be investigated being constructed from the individual one-dimensional image sequences. The dynamic factor can be set to B=100 in such line cameras, which means that a significantly broader grain distribution can be investigated than with a CCD matrix camera. However, the use of a line camera has the disadvantage that the projection areas of the measured particles are constructed from the line information under the assumption of a constant fall velocity of the relevant particles. This is not the case however, since during the scanning movement of the line camera the particles are undergoing an accelerated motion, and moreover particles of different size do not fall at the same velocity at the measurement site on account of air friction, but instead exhibit a velocity distribution. On account of these influencing factors, which are not negligible, such an apparatus does not operate with sufficient accuracy.

The object of the present invention is to improve an apparatus of the type mentioned at the beginning having regard to increasing the dynamic factor and the accuracy of the grain size determination.

SUMMARY OF THE INVENTION

This objective, together with advantageous modifications and developments of the invention, is achieved by the disclosures of the patent claims accompanying this description.

The basic concept of the invention is that the image collecting device comprises a plurality of electrooptical image recording units aligned onto the particle stream and having different mutually matched image scales for covering the whole measurement range of the apparatus.

The invention has the advantage that the electrooptical image recording unit having the larger image scale together with a correspondingly adjusted depth of focus records the larger particles, whereas the smaller particles of the particle stream are recorded by the electrooptical image recording unit having the smaller image scale and the depth of focus associated with this unit; the adopted division of work as regards the imaging of the projection areas of all the particles to be measured in the particle stream is correspondingly handled and processed in the computing unit, so that a uniform result of the grain distribution is obtained. Overall there is a substantially higher dynamic factor B on account of the expanded measurement range of the apparatus according to the invention.

According to one embodiment of the invention provision is made so that the electrooptical image recording unit with the smaller image scale is arranged at a shorter distance from the end of the metering device than the electrooptical image recording unit with the larger image scale. This has the advantage that in particular the smaller particles can already be recorded soon after leaving the metering device before the particles have reached their final fall velocity, having regard to the inevitably short exposure times. In this connection it can also be advantageous if the image collecting areas of the electrooptical image recording units intersect.

According to embodiments of the invention two or even three electrooptical image recording units with in each case different image scales may be aligned onto the particle stream, so that overall the dynamic factor a can be adjusted to the best possible value depending on the expected particle distribution in the particle stream.

With regard to the design of the electrooptical image recording units, according to one embodiment a plurality of one-dimensional image recording units, for example in the form of the already mentioned CCD line cameras, may also be used since different image scales can also be allocated to the line cameras and thus a division of work may be undertaken as regards the coverage of the differently sized particles.

According to a preferred embodiment of the invention the electrooptical image recording unit is designed as a two-dimensional image recording unit, in which connection in particular a CCD matrix camera may be used in each case. This has the advantage that a significantly higher dynamic factor B can be set for this category of instrument while retaining the benefits associated with the use of matrix cameras, in particular as regards their measurement accuracy.

In addition, according to an embodiment of the invention provision may be made so that with each of the matrix cameras a projection area of 3×3 image points is defined as lower image limit, where for example the matrix cameras with the smaller image scale has an image point size of 0.015 mm and the matrix cameras with the larger image scale has an image point size of 0.125 mm.

Where the metering device is provided with an adjustment device for alignment in the horizontal plane transverse to the particle stream, a demixing of the particle stream over the width of the metering device should be prevented so as to ensure a uniform grain distribution over the whole cross-section of the particle stream falling from the metering device. In this connection provision is made according to a further embodiment of the invention for the width of the metering device to correspond to the width of the image collecting area of the matrix camera having the larger image scale. The beat possible coverage of all individual particles is ensured by such an arrangement.

BRIEF DESCRIPTION OF THE DRAWINGS

One embodiment of the invention is described in more detail hereinafter with the aid of the drawings, in which:

FIG. 1 is a side view of a measuring apparatus;

FIG. 2 shows the camera arrangement according to FIG. 1, with the allocation of the image collecting areas in a single diagram.

DESCRIPTION OF THE PREFERRED EMBODIMENTS

The apparatus includes first of all a metering device 10 with a funnel 11, to which is connected a metering channel 12. The metering device roots on a substructure 13, which has an adjustment device 14 by means of which in particular the metering channel 12 can be aligned in the horizontal plane, and more specifically transverse to the particle stream 15 falling from the metering channel 12. A collection vessel 16 for collecting the particle stream 15 is arranged underneath the substructure 13.

The particle stream 15 falling from the metering channel 12 moves on account of the gravitational force acting on the particles between a light source 17 and an image collecting device, which in the illustrated embodiment comprises two CCD matrix cameras 18, 19. The upper matrix camera 18, at a smaller distance from the end of the metering channel 12, has a smaller image scale, while the lower matrix camera 19 is adjusted for a larger image scale. At can be seen in more detail from FIG. 2, the image collecting area 21 of the matrix camera 19 having the larger image scale and the image collecting area 20 of the matrix camera 18 having the smaller image scale intersect one another.

Within the scope of an embodiment the following image scales may for example be assigned to the matrix cameras 18 and 19; in the matrix camera 18 having the smaller image scale 18, the size of an image point (pixel) is for example set at 0.015 mm, the lower measurement limit being defined so that a particle in its projection area must cover at least an area of 3×3 image points in order to be recorded; the result is a lower measurement limit of 0.045 mm; the upper measurement limit is correspondingly set to as to cover 100×100 pixels, resulting in an upper measurement limit of 1.5 mm. If a commercially available CCD matrix camera having an image collecting area of 580×760 pixels is used, then an image collecting area of 8.7 mm×11.4 mm is obtained for the matrix camera 18.

An image point size of 0.125 mm is correspondingly assigned to the matrix camera 19, giving a lower measurement limit of 0.375 mm and an upper measurement limit of 12.5 mm. The result is an image collecting area in the particle plane of 72.5×95 mm. In this connection provision is made for a width of 75 mm when the metering channel 12 is inserted, so that the width of the image collecting area 21 is matched to the width of the metering channel 12.

A dynamic factor B=278 results from the data obtained from the aforementioned embodiment, which illustrates the substantially improved range of application of the apparatus according to the invention. By varying the site of the image points for the coverage of the projection areas of the individual particles, also significantly higher dynamic factors can even be achieved with other image scales.

The features of the subject matter disclosed in the preceding description, patent claims, abstract and drawing may be essential individually as well as in any arbitrary combinations for the realisation of the invention in its various modifications.

The specification incorporates by reference the entire disclosure of German priority document 198 02 141.0 Jan. 22, 1998.

The present invention is, in no way restricted to the specific disclosure of the specification and drawing, but also encompasses any modifications within the scope of the appended claims.

What is claimed is:

1. Apparatus for determining the particle size distribution and for characterizing the particle shapes of a particle mixture; said apparatus comprising:

a metering device (10) for classifying a particle mixture supplied in a particle stream (15) to said apparatus;

an optoelectronic measurement section comprising a light source (17) and an image collecting device (18, 19) aligned with one another, wherein the particle stream (15) is guided between said light source (17) and said image collecting device (18, 19);

said image collecting device (18, 19) comprising a plurality of electrooptical image recording units (18, 19) directed onto the particle stream (15) and having different image recording scales matched to one another to cover the whole measurement range of said apparatus;

a computing unit converting digital image points recorded by said recording units (18, 19) into a size determination of the particles.

2. Apparatus according to claim 1, wherein a first one of said electrooptical image recoding units (18) has a smaller image recording scale than a second one of said electrooptical image recording units (19), wherein said first electrooptical image recording unit (18) is closer to said metering device than said second electrooptical image recording unit (19).

3. Apparatus according to claim 1, wherein said electrooptical image recoding units (18, 19) have image collecting areas (20, 21) and wherein said image collecting areas (20, 21) intersect one another.

4. Apparatus according to claim 1, wherein two of said electrooptical image recording units (18, 19) are directed onto the particle stream (15).

5. Apparatus according to claim 1, wherein three of said electrooptical image recording units are directed onto the particle stream (15).

6. Apparatus according to claim 1, wherein said electrooptical image recording units (18, 19) are one-dimensional image recording units.

7. Apparatus according to claim 1, wherein said electrooptical image recording units (18, 19) are two-dimensional image recording units.

8. Apparatus according to claim 7, wherein said electrooptical image recording units comprise a CCD matrix camera (18, 19).

9. Apparatus according to claim 8, wherein said CCD matrix camera (18, 19) has a defined lower image limit of a projection area of 3×3 image points.

10. Apparatus according to claim 9, wherein a first one of said CCD matrix cameras (18) has a smaller image recording scale than a second one of said CCD matrix cameras (19), wherein said first CCD matrix camera (18) has an image point size of 0.015 mm and said second matrix camera (19) has an image point size of 0.125 mm.

11. Apparatus according to claim 10, wherein said metering device (10) has a width matching a width of an image collecting area (21) of said second CCD matrix camera (19).

12. Apparatus according to claim 1, wherein said metering device (10) has an adjustment device (14) for aligning said metering device (10) in a horizontal plane transverse to a direction of the particle stream.

* * * * *